(12) United States Patent
Grosse-Bley et al.

(10) Patent No.: US 6,617,314 B2
(45) Date of Patent: *Sep. 9, 2003

(54) INJECTABLE FORMULATIONS OF AVERMECTINS AND MILBEMYCINS

(75) Inventors: Michael Grosse-Bley, Köln (DE); Richard Kujanek, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/254,615

(22) PCT Filed: Sep. 8, 1997

(86) PCT No.: PCT/EP97/04867
§ 371 (c)(1),
(2), (4) Date: Mar. 10, 1999

(87) PCT Pub. No.: WO98/11902
PCT Pub. Date: Mar. 26, 1998

(65) Prior Publication Data
US 2002/0160967 A1 Oct. 31, 2002

(30) Foreign Application Priority Data
Sep. 18, 1996 (DE) .......................... 196 38 045

(51) Int. Cl.$^7$ ................................ A61K 31/70
(52) U.S. Cl. .......................... 514/28; 514/30; 514/341; 514/772; 514/943; 424/422
(58) Field of Search ............ 514/28, 772, 30, 514/341, 943; 424/422

(56) References Cited

U.S. PATENT DOCUMENTS

| | | | |
|---|---|---|---|
| 5,030,650 A | | 7/1991 | Buckwalter et al. ......... 514/450 |
| 5,055,486 A | | 10/1991 | Barden et al. .............. 514/450 |
| 6,001,822 A | * | 12/1999 | Wicks et al. .................. 514/63 |
| 6,001,858 A | * | 12/1999 | Sirinyan et al. ............ 514/341 |
| 6,013,636 A | * | 1/2000 | Harvey ........................ 514/30 |
| 6,063,394 A | * | 5/2000 | Grosse-Bley et al. ....... 424/422 |

FOREIGN PATENT DOCUMENTS

| | | | |
|---|---|---|---|
| CN | 1219393 | * | 6/1999 |
| RU | 2140737 | * | 11/1999 |

OTHER PUBLICATIONS

Pharmaceutical Dosage Forms and Drug Delivery Systems, edited by Ansel et al., publ. by Williams & Wilkins, pp. 110–116, 1995.*

* cited by examiner

Primary Examiner—Elli Peselev
(74) Attorney, Agent, or Firm—Susan M. Pellegrino

(57) ABSTRACT

The present application relates to injection formulations of avermectins and milbemycins based on a solvent mixture comprising sesame oil, medium-chain triglycerides, glycol esters or fatty acid esters and a further solvent from the group consisting of mono- or polyhydric aliphatic or aromatic alcohols and their derivatives (e.g. cyclic carbonates; acetates; acetals; ketals) or castor oil.

5 Claims, No Drawings

INJECTABLE FORMULATIONS OF AVERMECTINS AND MILBEMYCINS

The invention relates to new injection formulations of avermectins and milbemycins based on solvent mixtures which contain sesame oil.

Injection formulations of ivermectin are disclosed in EP-A 146 414. The formulations contain a solvent mixture of propylene glycol and glycerol formal in the ratio 60:40 v/v. It is known of propylene glycol that in certain concentrations it can cause local intolerabilities (see review: B. Kruss, Acta Pharm. Technol. 35(4) (1989) 187–196). The precipitation of the water-insoluble active compound ivermectin can also occur in the tissue around the administration site. Thus when using corresponding formulations marked swellings and tissue incompatibilities were observed at the injection sites, some of which only receded after several weeks.

Injection formulations of specific avermectins are disclosed in EP-A 393 890. They are oil formulations based on sesame oil and ethyl oleate in the ratio 90:10 v/v. These formulations are tolerable, but have the disadvantage that the solubility for avermectin/milbemycins is often inadequate to achieve a concentration of 1% m/v or higher which is desirable for use. As a rule, under elevated temperature conditions (T≧80° C.) supersaturated 1% n/v solutions are obtained, which permanently crystallize out again at lower temperatures.

Further injection formulations of avermectins are disclosed in EP-A 45 655. The formulations described there contain comparatively high amounts of emulsifiers and in some cases are not very tolerable.

Injection formulations of avermectins which contain triacetin (glycerol triacetate) are described in EP-A 413 538. In EP-A 535 734, injection formulations of avermectins based on triacetin and hydrogenated castor oil are described.

Further formulations for the injection of milbemycins and avermectins are described in EP-A 525 307. The formulations are prepared by fusing glycerol tristearates with the active compound and mixing with an oily neutral triglyceride and emulsifying using, for example, methylcellulose and salts. The average particle size in the microemulsion thus obtained should be between 25 and 300 μm.

The present invention relates to injection formulations of avermectins and milbemycins based on a solvent mixture comprising sesame oil, medium-chain triglycerides or glycol esters or fatty acid esters and a further solvent.

The formulations preferably contain:

1. active compound 0.2 to 5% m/v;

2. sesame oil 60 to 90% v/v;

3. medium-chain triglycerides or glycol esters or fatty acid esters 10 to 30% by volume;

4. 1 to 20% by volume of benzyl alcohol or propylene glycol or other suitable aliphatic or aromatic mono- or polyhydric alcohols and their derivatives (e.g. cyclic carbonates, acetates, acetals/ketals) or castor oil;

5. if appropriate, further auxiliaries.

The formulations according to the invention have an outstanding solubility for the active compounds.

The high viscosity of sesame oil can be adjusted to a desired low value by addition of medium-chain triglycerides or propylene glycol octanoate/decanoate or particularly ethyl oleate. Additionally, the solubility of the active compound can be improved, the viscosity further reduced and the bioavailability of the active compound improved by addition of relatively small volumes of hydrophilic solvents such as benzyl alcohol, propylene glycol or propylene carbonate with retention of a single-phase system. Castor oil is the only triglyceride which has a high solvent potential for the active compounds in question.

The active compounds employed in the formulations according to the invention are known.

Avermectins were isolated from the microorganism *Streptomyces avermitilis* as microbial metabolites (U.S. Pat. No. 4,310,519) and can occur essentially as a mixture consisting of the eight components $A_{1a}$, $A_{1b}$, $A_{2a}$, $A_{2b}$, $B_{1a}$, $B_{1b}$, $B_{2a}$ and $B_{2b}$ (I. Putter et al., Experentia 37 (1981) p. 963, Birkhäuser Verlag (Switzerland)). In addition the synthetic derivatives, in particular 22,23-dihydroavermectin $B_1$ (ivermectin), are also of interest (U.S. Pat. No. 4,199,569). Milbemycin B-41 D was isolated from *Streptomyces hygroscopicus* by fermentation (cf. "Milbemycin: Discovery and Development", I. Junya et al., Annu. Rep. Sankyo Res. Lab. 45 (1993), pp. 1–98; JP Pat. 8 378 549; GB 1 390 336).

The use of the avermectins, e.g. 22.23-dihydroavermectins $B_1$ (ivermectin) and milbemycins as endoparasiticides is known and is the subject of numerous patent applications and review articles (e.g. biological actions in: "Ivermectin and Abamectin", W. C. Campbell, Ed., Springer Verlag, New York, N.Y., 1989; "Avermectins and Milbemycins Part II" H. G. Davies et al., Chem. Soc. Rev. 20 (1991) pp. 271–339; chemical modifications in: G. Lukacs et al. (Eds.), Springer Verlag, New York, (1990), Chapter 3; Cydectin® [moxidectin and derivatives]: G. T. Carter et al., J. Chem. Soc. Chem. Commun. (1987), pp. 402–404); EP 423 445-A1) "Doramectin—a potent novel endectocide" A. C. Goudie et al., Vet. Parasitol. 49 (1993), pp. 5–15).

Avermectins and their derivatives which may be particularly emphasized are those of the general formula (I)

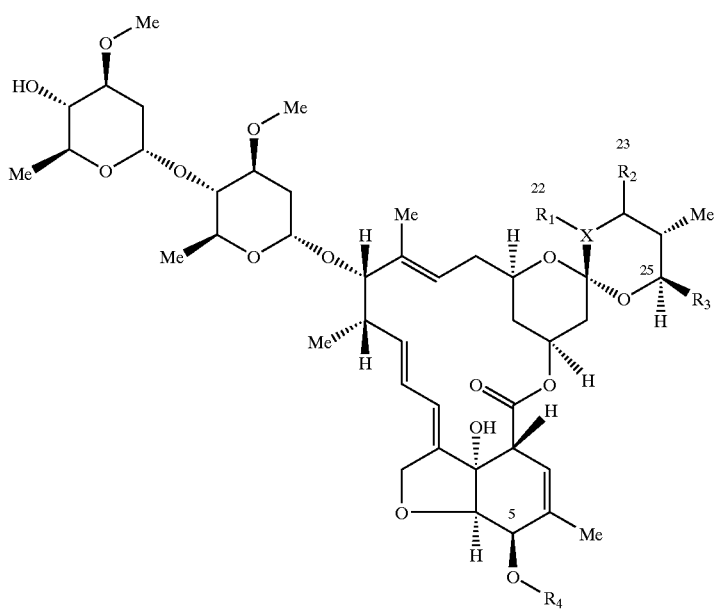

(I)

in which
the radicals $R^1$ to $R^4$ have the meaning indicated in Table 1 which follows and X can represent a single or double bond between the $C_{22}$- and $C_{23}$-positions ($-C_{22}R^1-X-C_{23}R^2-$)

If there is a double bond, there are no substituents ($R^1$, $R^2$) in the $C_{22}$- and $C_{23}$-positions.

TABLE 1

| Macrocyclic lactone | $-C_{22}R^1-X-C_{23}R^2-$ | $R^3$ | $R^4$ |
|---|---|---|---|
| Avermectin $A_{1a}$ | $-CH=CH-$ | -sec-Bu | $-Me$ |
| Avermectin $A_{1b}$ | $-CH=CH-$ | -iso-Pr | $-Me$ |
| Avermectin $A_{2a}$ | $-CH_2-CHOH-$ | -sec-Bu | $-Me$ |
| Avermectin $A_{2b}$ | $-CH_2-CHOH-$ | -iso-Pr | $-Me$ |
| Avermectin $B_{1a}$ | $-CH=CH-$ | -sec-Bu | $-H$ |
| Avermectin $B_{1b}$ | $-CH=CH-$ | -iso-Pr | $-H$ |
| Avermectin $B_{2a}$ | $-CH_2-CHOH-$ | -sec-Bu | $-H$ |
| Avermectin $B_{2b}$ | $-CH_2-CHOH-$ | -iso-Pr | $-H$ |
| 22.23-dihydroavermectin $B_{1a}$ | $-CH_2-CH_2-$ | -sec-Bu | $-H$ |
| 22.23-dihydroavermectin $B_{1b}$ | $-CH_2-CH_2-$ | -iso-Pr | $-H$ |
| Doramectin | $-CH=CH-$ | $-Chx$ | $-H$ |

22.23-Dihydroavermectin $B_1$ is ivermectin; sec-Bu = secondary butyl; iso-Pr = isopropyl; Chx = cyclohexyl; —Me = methyl As a rule, the avermectins and 22,23-dihydroavermectins $B_1$(ivermectin) of the general formula (I) are employed as mixtures. Of particular interest in this connection is the product abamectin, which contains the avermectins $B_1$, and their hydrogenation products, the 22,23-dihydroavermectins $B_1$ (ivermectin).

The compounds of the macrocyclic lactones marked with "b" which in the $C_{25}$-position have an iso-propyl radical, do not necessarily have to be separated from the "a" compounds, which have a sec-butyl group in the $C_{25}$-position. Generally the mixture of both substances, consisting of >80% sec-butyl derivative ($B_{1a}$) and <20% iso-propyl derivative ($B_{1b}$), is isolated, and can be used according to the invention. Additionally, in the stereoisomers the substituents in the $C_{13}$- and $C_{23}$-positions can be arranged on the ring system both in the α- and β-positions, i.e. relocated above or below the plane of the molecule. In each case, all stereoisomers are taken into account according to the invention.

The milbemycins may be mentioned particularly. The milbemycins have the same macrolide ring structure as the avermectins or 22,23-dihydroavermectins $B_1$ (ivermectin), but carry no substituents (i.e. missing oleandrose disaccharide fragment) in position 13 ($R^5$=hydrogen).

As examples of milbemycins from the class of macrocyclic lactones, the compounds having the general formula (II) may be mentioned

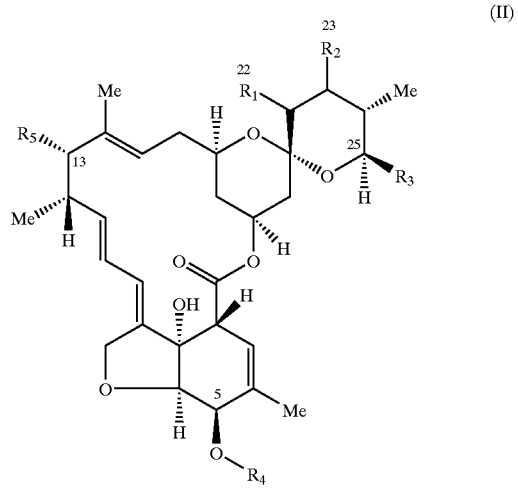

(II)

in which
the radicals $R^1$ to $R^4$ have the meaning indicated in Table 2 which follows:

TABLE 2

| Macrocyclic lactone | $R^1$ | $R^2$ | $R^3$ | $R^4$ | $R^5$ |
|---|---|---|---|---|---|
| Milbemycin B41 D | $-H$ | $-H$ | -iso-Pr | $-H$ | $-H$ |

TABLE 2-continued

| Macrocyclic lactone | $R^1$ | $R^2$ | $R^3$ | $R^4$ | $R^5$ |
|---|---|---|---|---|---|
| Nemadectin | —H | —OH | CH=C(Me)–CH(Me)– with Me,Me branches | —H | —H |
| Moxidectin | —H | =N—O—Me | CH=C(Me)–CH(Me)– with Me,Me branches | —H | —H | iso-Pr = isopropyl

The active compounds which may be very particularly emphasized are avermectin $B_{1a}/B_{1b}$ (abamectin), 22,23-dihydroavermectin $B_{1a}/B_{1b}$ (ivermectin), doramectin, moxidectin.

The active compounds are present in the formulations according to the invention in concentrations from 0.2 to 5%, preferably from 0.5 to 2%, particularly preferably 1% m/v.

The sesame oil employed in the formulations according to the invention (60 to 90% v/v) is known.

The viscosity depressants, in particular ethyl oleates, employed in the formulations according to the invention are known.

Further solvents which are good and can be employed as a constituent of preparations for injection are especially benzyl alcohol, propylene glycol, glycerol formal, propylene carbonate, triacetin, Myvacete® (trademark of Eastman), propylene glycol diacetate, polyethylene glycol 400, tetraglycol and castor oil. Benzyl alcohol (1 to 5% v/v) and castor oil (10 to 20% v/v) are particularly preferred.

The solubility of ivermectin in benzyl alcohol is >40% by weight and in castor oil ~4% by weight.

Further additives to the formulations according to the invention are stabilizers such as butylhydroxyanisole (BHA), butylhydroxytoluene (BHT) or propyl gallate of up to 1000 ppm in total. Particularly suitable stabilizer combinations and concentrations are, for example, 100 ppm of BHA or 100 ppm of BHA plus 150 ppm of propyl gallate or 200 ppm of BHA plus 100 ppm of propyl gallate.

The viscosity of the formulations according to the invention is between 20 and 60 mPa.s (20° C.), preferably between 25 and 55 mPa.s (20° C.), particularly preferably between 30 and 51 mPa.s (20° C.).

The following examples illustrate the invention.

Note:

$$v/v = \frac{volume}{volume} \text{ corresponds to percent by volume}$$

$$m/v = \frac{mass}{volume}$$

1% m/v means, for example 10 mg of active compound in 1 ml of solution.

EXAMPLE 1

| | |
|---|---|
| Sesame oil | q.s. 100% v/v |
| Ethyl oleate | 10% v/v |
| Benzyl alcohol | 2% v/v |
| Ivermectin | 1% m/v |
| Butylhydroxyanisole (BHA) | 100 ppm (Δ 0.01% m/v) |
| Density: | 0.922 g/ml |
| Viscosity: | 44 mPa.s at 20° C. |
| | 85 mPas at 5° C. |
| | 24 mPa.s at 39° C. |

EXAMPLE 2

| | |
|---|---|
| Sesame oil | q.s. 100% v/v |
| Ethyl oleate | 20% v/v |
| Castor oil | 10% v/v |
| Ivermectin | 1% m/v |
| Butylhydroxyanisole (BHA) | 100 ppm (Δ 0.01% m/v) |
| Density: | 0.927 g/ml |
| Viscosity: | 38 mPa.s at 20° C. |
| | 83 mPa.s at 5° C. |

General Preparation Procedure for Examples 1 and 2 as Sterile Solutions for Injection Sesame oil and ethyl oleate, provided with 100 ppm of BHA are weighed into a stainless steel container and homogenized with stirring. The ivermectin, dissolved or partially dissolved in benzyl alcohol or castor oil, is introduced with further stirring. The mixture is warned to 40 to 60° C. in order to guarantee the rapid, complete dissolution of the active compound (all under aeration with nitrogen). The mixture is then sterile-filtered at the same temperature through a 0.22 μm filter (as a rule a 0.45 μm or 1 μm filter is preinserted). Aseptic dispensing into brown glass bottles follows.

The formulations prepared in this way are outstandingly tolerable when used in cattle. They are additionally stable on storage at temperatures of 60° C. over at least 6 weeks.

What is claimed is:

1. An injectible formulation comprising:

1. avermectin or milbemycin 0.2 to 5% m/v;
2. sesame oil 60 to 90% v/v;
3. 10 to 30% by volume of medium-chain triglycerides or glycol esters or fatty acid esters;
4. 1 to 20% co-solvent from the group consisting of mono- or polyhydric aliphatic or aromatic alcohols and their derivatives selected from the group consisting of cyclic carbonates, acetates, acetals and ketals, and castor oil;
5. optionally auxiliaries.

2. The formulation according to claim 1, of the following composition:

0.2 to 5% m/v of an avermectin or milbemycin in a solvent mixture consisting of 60 to 90% v/v of sesame oil, 10 to 30% v/v of ethyl oleate or fractionated coconut oil containing triglycerides of capyrlic acid and capric acid known as MIGLYOL® 812 or propylene glycol caprylic acid capric acid diester known as MIGLYOL® 840, 1 to 5% v/v of benzyl alcohol or 10 to 20% v/v of castor oil, and optionally up to 1000 ppm of stabilizers.

3. The formulation according to claim 1, of the following composition:

1% in/v of avermectin, 65 to 90% v/v of sesame oil, 10 to 20% v/v of ethyl oleate, 1 to 3% v/v of benzyl alcohol or 10% v/v of castor oil, and optionally up to 500 ppm of a stabilizer.

4. A process for preparing the formulation according to claim 1, comprising partially dissolving the avermectin or milbemycin in castor oil or benzyl alcohol and adding the remaining solvents in the formulation according to claim 1 or dissolving the avermectin or milbemycin in a mixture of the solvents.

5. A process for solubilizing an avermectin or milbemycin comprising adding castor oil or benzyl alcohol as a solubilizer in the formulation according to claim 1.

* * * * *